(12) United States Patent
Hartman et al.

(10) Patent No.: US 8,923,978 B1
(45) Date of Patent: Dec. 30, 2014

(54) EXERCISE DEVICE WITH STIMULATION BASED ON VOLITIONAL CONTRIBUTION AND RELATED METHODS

(75) Inventors: Eric C. Hartman, Lexington, KY (US); L. Gentry Barnett, Lexington, KY (US); Tarik S. Aweimrin, Lexington, KY (US); John D. Alton, Versailles, OH (US)

(73) Assignee: Customkynetics, Inc., Versailles, KY (US)

( * ) Notice: Subject to any disclaimer, the term of this patent is extended or adjusted under 35 U.S.C. 154(b) by 316 days.

(21) Appl. No.: 13/450,558

(22) Filed: Apr. 19, 2012

Related U.S. Application Data (60) Provisional application No. 61/477,006, filed on Apr. 19, 2011.

(51) Int. Cl.
*A61N 1/00* (2006.01)

(52) U.S. Cl.
USPC .......................................................... 607/48

(58) Field of Classification Search
USPC .......................................................... 607/48
See application file for complete search history.

(56) References Cited

U.S. PATENT DOCUMENTS

| | | |
|---|---|---|
| 4,421,336 A | 12/1983 | Petrofsky et al. |
| 4,499,900 A | 2/1985 | Petrofsky et al. |
| 4,509,509 A | 4/1985 | Bouvet et al. |
| 4,520,827 A | 6/1985 | Wright et al. |
| 4,809,696 A | 3/1989 | Laenger et al. |
| 4,838,272 A | 6/1989 | Lieber |
| 4,863,157 A | 9/1989 | Mendel et al. |
| 5,328,424 A | 7/1994 | Greco |
| 5,507,788 A | 4/1996 | Lieber |
| 6,042,518 A | 3/2000 | Hilderbrandt et al. |
| 6,152,855 A | 11/2000 | Dean, Jr. et al. |
| 6,361,479 B1 | 3/2002 | Hilderbrandt et al. |
| 6,666,799 B2 | 12/2003 | Hilderbrandt et al. |
| 6,960,155 B2 | 11/2005 | Chien et al. |
| 7,260,436 B2 | 8/2007 | Kilgore et al. |
| 7,381,192 B2 | 6/2008 | Brodard |
| 2004/0127954 A1 | 7/2004 | McDonald, III |
| 2004/0172093 A1 | 9/2004 | Rummerfield |
| 2005/0015118 A1 | 1/2005 | Davis et al. |
| 2006/0247095 A1 | 11/2006 | Rummerfield |
| 2006/0293156 A1 | 12/2006 | Trees |
| 2007/0208392 A1* | 9/2007 | Kuschner et al. ............... 607/48 |

FOREIGN PATENT DOCUMENTS

GB      2392110      2/2004

* cited by examiner

*Primary Examiner* — Robert N Wieland
(74) *Attorney, Agent, or Firm* — King & Schickli, PLLC (57) ABSTRACT

A device is provided for use in performing an exercise involving at least one lower extremity of a human subject. The device may include a base including at least one moveable receiver adapted for engaging the at least one lower extremity. At least one stimulator is provided for applying electrical stimulation at a first level to at least one muscle for causing movement of the at least one lower extremity. A controller is also provided for adjusting the stimulator to apply stimulation to the at least one muscle at a second level based on a volitional movement by the human subject.

11 Claims, 10 Drawing Sheets

EXERCISE DEVICE WITH STIMULATION BASED ON VOLITIONAL CONTRIBUTION AND RELATED METHODS

This application claims the benefit of U.S. Provisional Patent Application Ser. No. 61/477,006, filed Apr. 19, 2011, the disclosure of which is incorporated herein by reference.

STATEMENT OF GOVERNMENT SUPPORT

This invention was supported by a grant from the National Institute of Health under contract number 1R43HD065383-01. The government may have certain rights in this invention. This invention was made with an award from the Kentucky Cabinet for Economic Development, Department of Commercialization and Innovation, under Grant Agreement KSTC-184-512-10-095 with the Kentucky Science and Technology Corporation.

COPYRIGHT STATEMENT

A portion of the disclosure of this document contains material subject to copyright protection. No objection is made to the facsimile reproduction of the patent document or this disclosure as it appears in the Patent and Trademark Office files or records, but any and all rights in the copyright(s) are otherwise reserved.

TECHNICAL FIELD

The present disclosure relates to the human exercise and rehabilitation arts and, more particularly, to devices for facilitating the performance of an exercise with adaptive stimulation and related methods.

BACKGROUND OF THE INVENTION

Facilitating exercise using externally applied, transcutaneous stimulation, including by sending electrical pulses to contract or otherwise activate the targeted or involved muscles, is known in the art. Typically, the electrical pulses applied are generated by an external stimulator, and travel through associated wires to one or more electrode pairs placed on the skin adjacent the muscle(s) to be contracted. The electricity passing through the skin causes the targeted muscle fibers to activate or contract, even without voluntary control by the subject. Accordingly, such stimulation is frequently used in situations where the subject is incapacitated or otherwise unable to control function of the muscles, such as in the event of an injury to the brain or associated portion of the nervous system.

Despite the widespread past use of electrical stimulation for exercising muscles, certain limitations in the application of this technology and the results produced remain. Specifically, the application of the stimulation is often based on "ramp and hold" type patterns that are externally applied based on timing. The application of such a pre-determined level of stimulation at a fixed interval is usually divorced from any volitional movement of the subject, and instead is applied by the clinician in an attempted synchronization with the exercise movement. Aside from being extremely unnatural, the benefit afforded by such an approach is not maximized in terms of encouraging the subject to make volitional contributions to the exercise.

Accordingly, a need is identified for a manner in which to apply an electrical stimulation to a subject based on a volitional exercise motion by that subject. Further, a need is identified for a manner in which to combine the benefits achieved through such a coordinated electrical stimulation based on volitional movement in a stepping exercise.

SUMMARY OF THE INVENTION

In one aspect, this disclosure relates to a device for use in performing an exercise involving at least one lower extremity of a human subject. The device comprises a base including at least one moveable receiver adapted for engaging the at least one lower extremity, at least one stimulator for applying electrical stimulation at a first level to at least one muscle for causing movement of the at least one lower extremity, and a controller for adjusting the stimulator to apply stimulation to the at least one muscle at a second level based on a volitional movement by the subject.

The device may further include a sensor for sensing a force exerted by the subject during the volitional movement, wherein the controller adjusts the stimulator based on the sensed force. The sensor may be associated with a second receiver for receiving an upper extremity of the subject. In one aspect of this embodiment, the second receiver may comprise a handlebar carried by the base, and the sensor may comprise a load cell associated with the handlebar. In one embodiment, the load cell may be associated with a grip of the handlebar.

In another aspect of this embodiment, the base may include a pair of receivers, each for receiving one of the lower extremities of the subject.

In another aspect, the receiver may be associated with a sensor for sensing a force resulting from the movement of the lower extremity.

In a further aspect of this embodiment, the base may include a pair of receivers for the upper extremities and a pair of receivers for the lower extremities, each of the receivers associated with a sensor for sensing a force resulting from the movement of the corresponding upper or lower extremity. The controller may be adapted for adjusting an intensity of the stimulation applied to achieve a desired ratio of force exerted by the upper extremities to the lower extremities. In another aspect of this embodiment, the controller may be adapted for receiving an input value of a desired lower extremity involvement ($LEI_{Desired}$) and for measuring an actual lower extremity involvement ($LEI_{Actual}$), and for comparing the $LEI_{Desired}$ with the $LEI_{Actual}$ and adjusting the intensity of the stimulator to synchronize $LEI_{Desired}$ with the $LEI_{Actual}$.

In still another aspect of the present embodiment, the controller may be further adapted for controlling a rate at which the intensity of the stimulator is adjusted.

The device of the present embodiment may further include at least one stop located at a distal end of a path of travel of the receiver for retarding movement to simulate a foot making contact with the ground.

In another aspect, the controller is adapted to temporarily reduce an intensity of the stimulation and then gradually allow the intensity to increase. The controller may also provide a stimulation pattern based on the volitional movement.

In a further embodiment, the disclosure relates to an improvement in an exercise device, the improvement comprising an electrical stimulator and a controller for controlling the intensity of electrical stimulation applied by the stimulator to a first limb based on movement of a second limb. The controller may synchronize the application of the electrical stimulation to the first limb based on movement of the second limb.

Another embodiment of the disclosure relates to a device for performing a recumbent stepping exercise, wherein the improvement comprises an electrical stimulator and a controller for controlling the electrical stimulation applied by the stimulator to a first limb based on movement of a second limb. The controller may synchronize the application of the electrical stimulation to the first limb based on movement of the second limb. In another aspect of this embodiment, the controller may control the intensity of the electrical stimulation to the first limb based on movement of the second limb.

An additional embodiment of the disclosure relates to a device for use by a human subject in performing a recumbent stepping exercise using their arms, legs, hips, knees and feet with the assistance of stimulation. The device comprises a base, a seat supported by the base for receiving the subject, a pair of receivers adapted for independently engaging the subject's feet, the receivers constrained for moving alternately and relative to the base along a path of travel in a stepping pattern between a first, extended position with the corresponding leg at least partially bent and the corresponding knee positioned farther from the subject's upper torso and a second, retracted position with the corresponding leg more bent than in the first position and positioned closer the subject's upper torso, such that the hip joint corresponding to each leg is being exercised during the stepping pattern, a stimulator adapted for electrically stimulating at least one muscle of at least one of the subject's legs, and a controller for controlling the stimulator based on the movement of at least one of the subject's arms. In one aspect, the device further includes at least one handlebar for engaging an upper extremity of the subject, said handlebar associated with a sensor.

In the invention of any of the above embodiments, the controller may control the stimulator to provide a pre-determined stimulation pattern based on the movement of the upper extremity or arm of the subject. The controller may provide the pre-determined stimulation pattern based on empirical data associated with a different subject performing the stepping exercise without the application of stimulation.

Still a further embodiment of the disclosure relates to a method of providing electrical stimulation to a human subject. The method comprises applying electrical stimulation at a first level to at least one muscle associated with movement of the subject's legs, and adjusting the stimulation to a second level based on a volitional movement of the subject. In one aspect, the adjusting step comprises adjusting the stimulation based on the volitional movement of one of the subject's arms. In another aspect, the step of adjusting the intensity of the electrical stimulation corresponds to a force exerted by the arm.

This method may further comprise the step of positioning the subject in a recumbent cross-training exercise machine with a pair of upper receivers for engaging the subject's upper limbs and a set of lower receivers for engaging the subject's lower limbs. Additionally, the method may include the step of providing at least one stop located at a distal end of the path of travel of at least one of the lower receivers for retarding the movement of said lower receiver to simulate a foot making contact with the ground.

Yet another embodiment of the disclosure relates to a method of providing electrical stimulation to a human subject during a stepping exercise. The method comprises applying electrical stimulation to at least one muscle associated with the movement of at least one of the subject's legs, and sensing a volitional movement of the subject and adjusting the applied stimulation based on the sensed volitional movement. The sensing step may comprise sensing the volitional movement of the subject's arm.

Another embodiment relates to a method of providing electrical stimulation to a human subject during a stepping exercise, said method comprising applying electrical stimulation to at least one muscle associated with the movement of at least one of the subject's legs, and sensing a force generated as the result of the movement of at least one of the subject's arms and adjusting the applied stimulation based on the sensed force.

A further embodiment involves a method for providing a device for use by a human subject in performing a recumbent stepping exercise using their lower extremities. This embodiment comprises providing a base including at least one moveable receiver adapted for engaging the at least one lower extremity, providing at least one stimulator for applying electrical stimulation at a first level to at least one muscle for causing movement of the at least one lower extremity, and providing a controller for adjusting the stimulator to apply stimulation to the at least one muscle at a second level based on a volitional movement by the subject.

A final embodiment discloses a method of performing a recumbent stepping exercise on a human subject with full or partial loss of leg muscle control. This method comprises electrically stimulating at least one muscle for effecting leg movement at a predetermined level as the legs move alternately along a path of travel between a first position and a second, extended position during the stepping exercise, sensing a parameter corresponding to movement of the subject's arms, adjusting the level of electrical stimulation to a revised level based on the sensed parameter, and electrically stimulating at least a portion of the leg muscles at the revised level.

DETAILED DESCRIPTION OF THE INVENTION

Figure 1A:
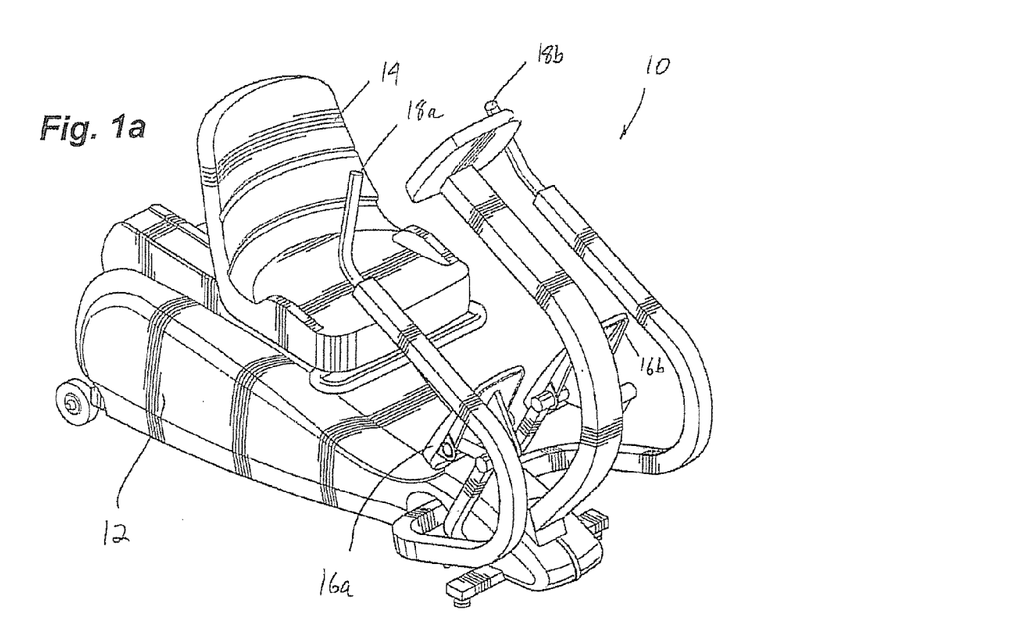
FIG. 1a is a perspective view of the exercising device forming one embodiment according to the present disclosure.
Figure 1B:
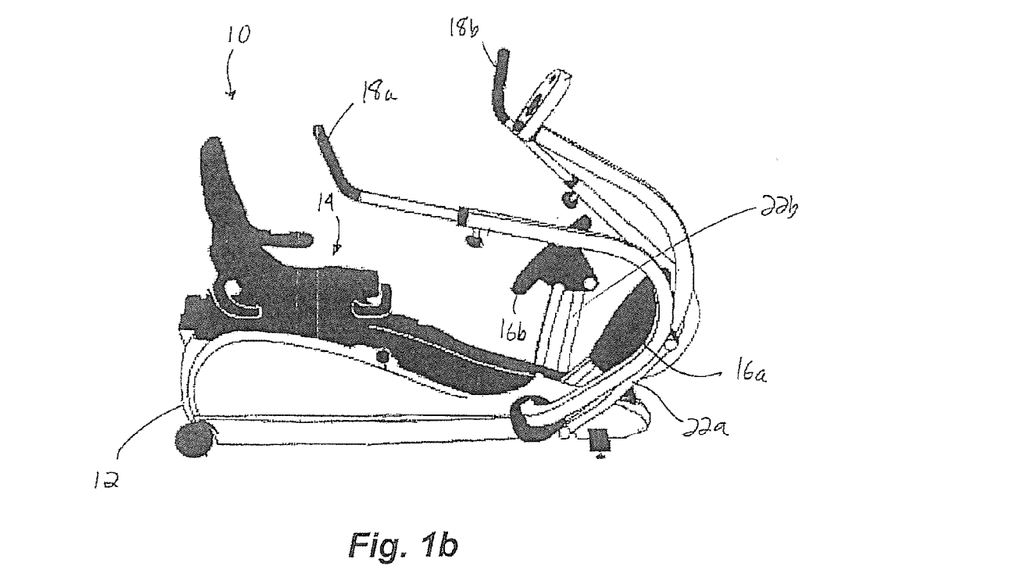
FIG. 1b is a is a side elevational view thereof.

Reference is now made to FIGS. 1a and 1b, which schematically depict an exercise device 10 forming one aspect of the disclosure. In one possible embodiment, as illustrated, the device 10 facilitates performing an alternating leg extension, or "stepping," exercise while the subject is seated (sometimes referred to in the vernacular as "recumbent stepping"). The device 10 shown in FIG. 1 is distributed commercially by NuStep, Inc. of Ann Arbor, Mich. under the model number TRS 4000. Such a device 10 is also generally described and shown in U.S. Pat. Nos. 6,042,518; 6,361,479; 6,666,799; D421,075, and 7,996,080, the disclosures of which are each incorporated herein by reference. However, it should be appreciated that various aspects of the invention disclosed herein may be applied to other types of exercise devices, without limitation.

The illustrated device 10 comprises a base 12 supporting an associated seat 14 in an elevated fashion. Together, these components of the device 10 support the exercise subject (see FIGS. 6 and 7) above the ground sitting upright in a stable, secure fashion.

The base 12 also provides support for pivotally mounted, bi-lateral foot receivers, such as plates 16a, 16b, for receiving the left and right feet of the exercise subject when seated in seat 14. The plates 16a, 16b are constrained to allow for reciprocal movement with the legs approximately 180° out of phase (that is, the movement of one plate by one leg toward the extended position moves the other plate, and hence the corresponding leg, toward the retracted position). This may be accomplished by using a linkage, belt, or like structure to connect the footplates 16a, 16b to a rotary part (which may be associated with an inertial element and a clutch), such that the rotation in alternating directions alternates the linear movement of these plates.

Preferably, the seat 14 is mounted to the base 12 in a manner that permits it to be adjusted to and fro with respect to a horizontal plane, or generally parallel to level ground. This allows for the necessary adjustments to be made to ensure that the desired range of motion can be achieved with comfort for a particular subject. The seat 14 may also be adapted to swivel in order to make it easier for the subject to assume the seated position.

Figure 2A:
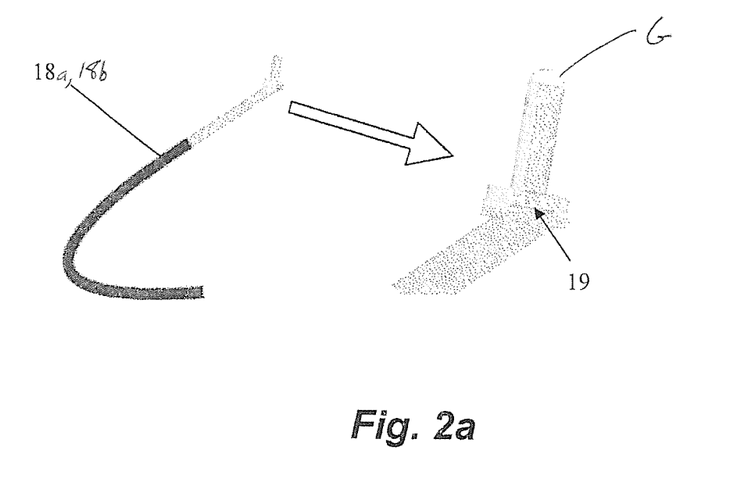
FIG. 2a is a side view of an upper receiver.

Also supported by the base 12 are receivers for the subject's upper extremities, such as handlebars 18a, 18b. Preferably, these handlebars 18a, 18b are mounted to also allow for reciprocal movement of the arms during the stepping exercise. With reference to FIG. 2a, each handlebar 18a, 18b may be associated with a sensor, such as for example a load cell 19, for measuring a force exerted on the handlebar. A handgrip G may also be provided for receiving the subject's hand, and the load cell 19 may be positioned at the interface between the handgrip G and the handlebar 18a, 18b for measuring the corresponding force exerted by the upper extremity during the exercise movement.

Figure 2B:
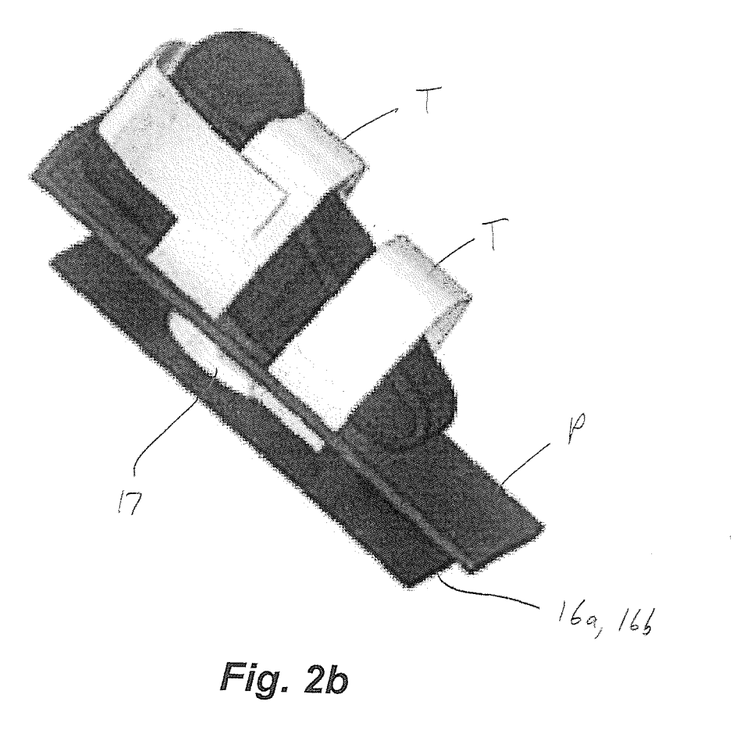
FIG. 2b is a perspective view of a footplate.

It may also be desirable in some application to acquire a measure of the force exerted on each footplate 16a, 16b. Thus, as shown in FIG. 2b, each plate 16a, 16b may be associated with a sensor, such as a load cell 17 for measuring a force exerted by the foot on the plate 16a, 16b. This load cell 17 may be positioned between the existing footplate 16a, 16b and a modified plate P including straps S adapted for securing the foot of the subject, which may be necessary in situations where lower extremity motor control is lacking.

The device 10 also includes a stop 20 providing an engagement surface for stopping movement of the plates 16a, 16b for receiving the subject's feet. In the illustrated embodiment, and with reference to FIGS. 2 and 3, this stop 20 forms part of the base 12 adjacent to pivotally mounted plate supports 22a, 22b (which may comprise a linkage formed of one or more bars) supporting the plates 16a, 16b. The stop 20 includes at least one, and preferably a pair of spaced bumpers 24a, 24b for engaging the respective support 22a, 22b at the end, or bottom of the range of motion.

Figure 3:
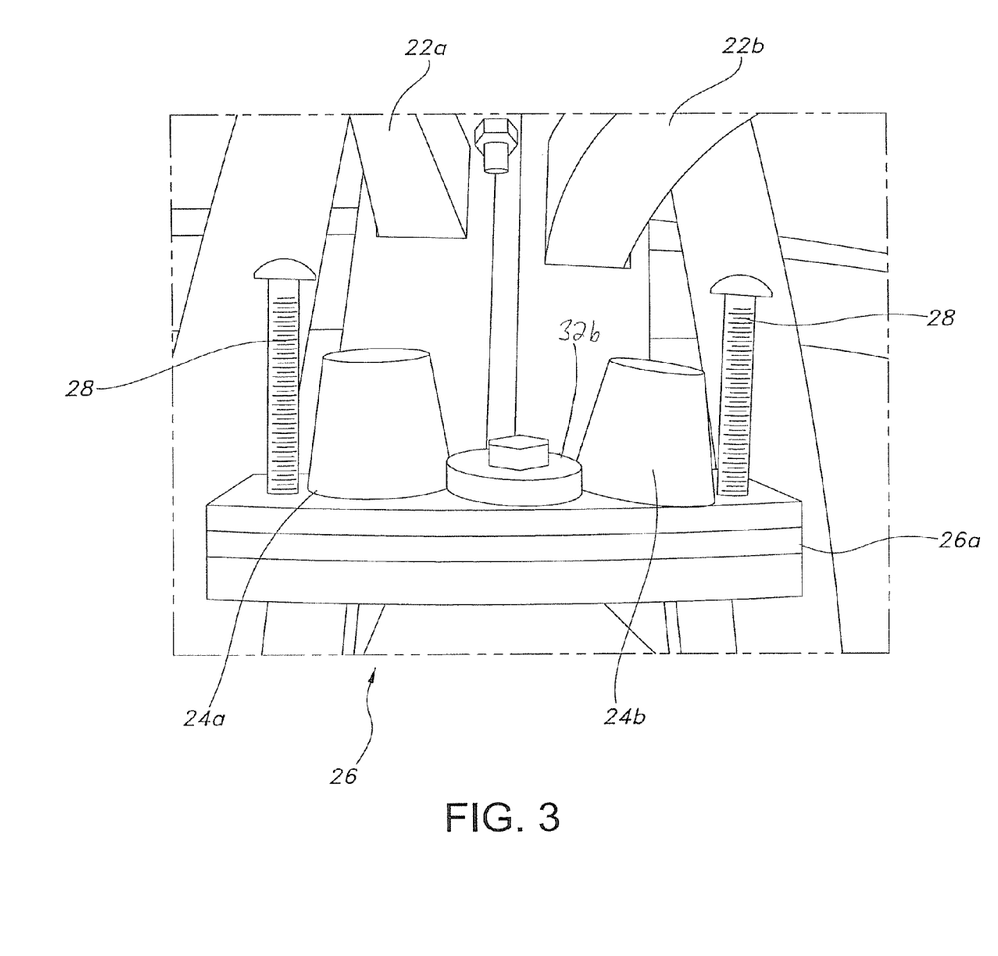
FIG. 3 is a front perspective of the stops of one embodiment of the disclosure.

It may be desirable to limit the range of motion such that the knee joint does not lock during the stepping exercise, since it is generally not possible to unlock this joint through the use of stimulation. To ensure that the knees do not lock, the stop may comprise a spacer assembly 26 including a plurality of spacers, such as plates 26a . . . 26n, removably associated with the assembly, such as by using fasteners 28. As should be appreciated, adding or removing the spacer plates 26a allows for the maximum movement of the supports 22a, 22b at the end of the range of motion, as desired for a particular subject performing the stepping exercise with or without stimulation.

Figure 4:
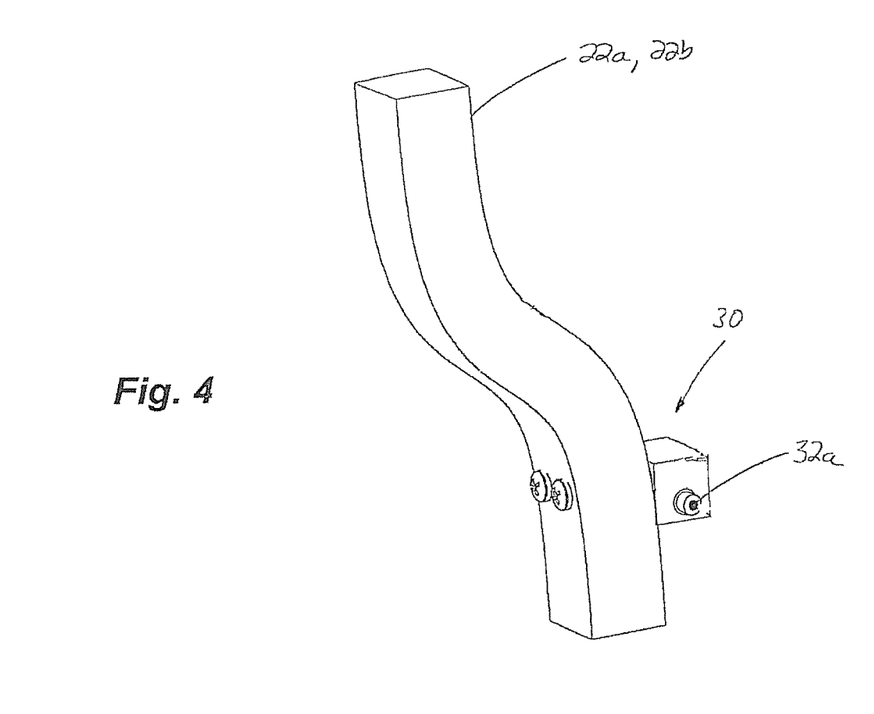
FIG. 4 is a perspective view of a motion sensor of one embodiment of the disclosure.

The preferred embodiment employs a position sensor 30, which may take the form of a magnetic proximity switch 32a mounted to each support 22a, 22b (see FIG. 4). A corresponding magnet 32b is mounted in a stationary fashion near the end of the range of motion, such as on or adjacent the stop (see FIG. 3). As a result, the position of the foot plates 16a, 16b for at least one point in range of motion is known (that is, the magnetic switch 32a is closed as the result of being in the proximity of the magnet 32b at the end of the range of motion of each leg when the corresponding support 22a, 22b engages the stop).

Figure 5A:
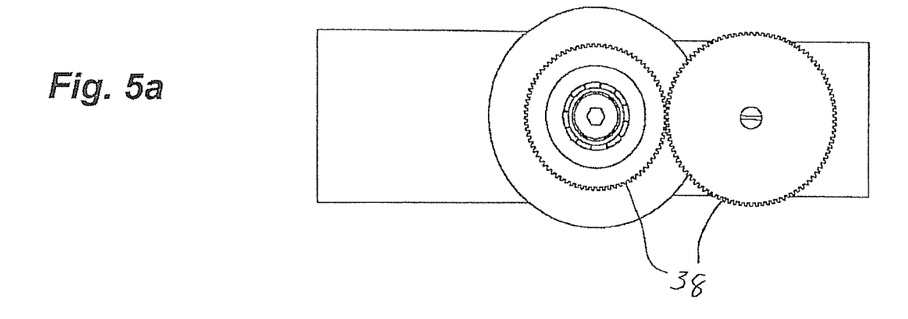
FIG. 5a is a side elevation view of gears in accordance with one embodiment of the disclosure.
Figure 5B:
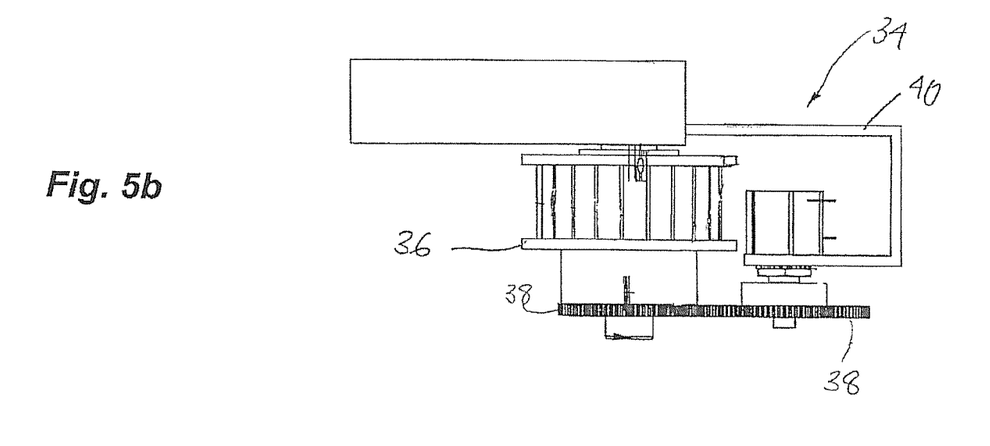
FIG. 5b is a top plan view thereof.

With reference to FIGS. 5a and 5b, the preferred embodiment further includes a motion sensor 34, such as a potentiometer, associated with a rotary part 36 of the device 10 that moves in a cyclical fashion in response to the relative movement of the plates 16a, 16b during the reciprocating movement of the legs. This sensor 34 may form part of a sensor assembly, which includes gears 38 for transmitting the movement from the rotary part 36 to the potentiometer. A corresponding bracket 40 for associating with the base 12 or a corresponding stable support structure provides the desired mounting of the various components.

Figure 6:
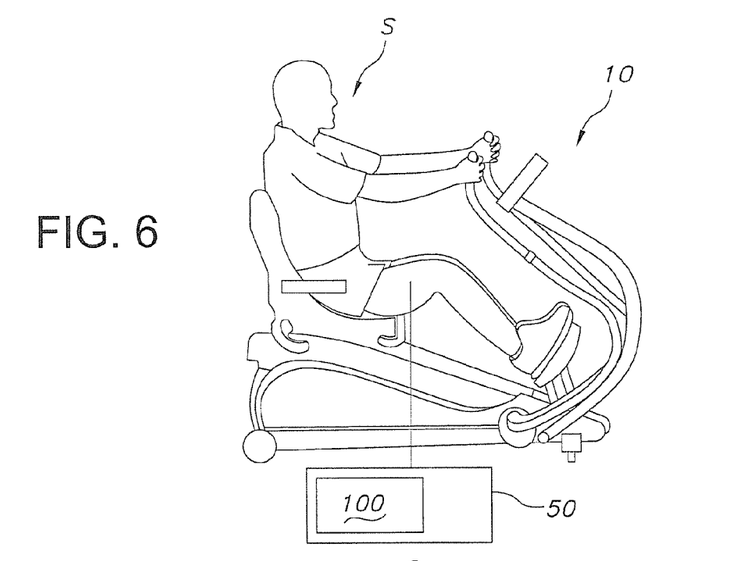
FIG. 6 is a perspective view of an individual engaging the device of the disclosure.
Figure 7:
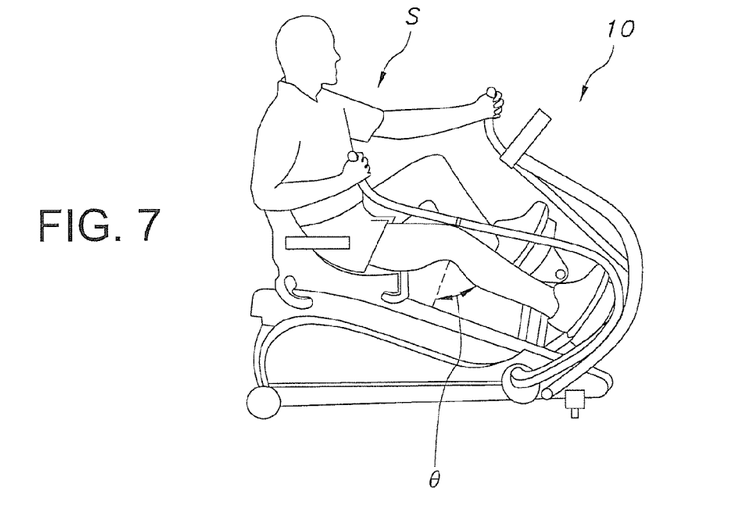
FIG. 7 is a perspective view of an individual using the device of the disclosure.

In one mode of operation, and with reference now to FIGS. 6 and 7, a subject S having full or partial loss of control of their leg muscles or otherwise in need of stimulation-assisted exercise is positioned on the seat 14 with their feet engaging the corresponding receivers (plates 16a, 16b) and their hands engaging the corresponding receivers (handlebars 18a, 18b) in the manner shown in FIG. 6. The stop may be adjusted if necessary to ensure that at the maximum range of motion of each leg, such as the extended leg in FIG. 7, the flexion angle θ of the bent knee in the extended position is such that the leg is not fully extended.

As shown in FIGS. 6 and 7, in practice, as the right hand is retracted toward the body and the left hand is extracted away from the body, the right foot is extracted away from the body and the left foot is retracted toward the body. These positions are then reversed as the subject S progresses through a cycle of the exercise. A cycle is defined as the period from subsequent fully retracted desired positions of a single footplate.

Once the subject S is properly positioned, one or more of the muscles for contributing to movement of the legs (e.g., the extensors and flexors) are alternately electrically stimulated through one or more pairs of strategically placed electrodes using an external stimulator 50 of a type generally known in the art (such as, for example, the CK-200 device available from customKYnetics, Inc.). This stimulation contracts the necessary muscles as required to cause or otherwise forcibly assist the stimulated leg in extending through a range of motion from a bent to an extended condition. Specifically, the leg to which stimulation is applied, if initially in generally relaxed or passive, bent resting position moves toward an active position in which the leg is less bent, such that the knee joint moves from closer to the upper torso to farther away from the upper torso. The procedure is then repeated for the opposite leg, which as a result of the reciprocal nature of the device 10 would at that time be in the generally relaxed or passive, bent resting position.

As noted above, the exemplary approach for purposes of illustrating one preferred embodiment of the invention generally involves placement of electrodes as necessary to stimulate the muscles to effect movement of the lower extremities (e.g., the quadricep, hamstring, and gluteus maximus). As should be appreciated, the particular muscles stimulated, the location of the electrodes, the level of stimulation (that is, the amount of energy supplied per pulse), and the pulse parameters (that is, the frequency and amplitude) necessary to cause the subject to involuntarily extend their legs in such a manner may vary depending on the particular application or situation. The adjustment and application of such parameters is believed to be fully within the purview of one of ordinary skill in the electrically stimulated exercise arts.

During this dynamic loading cycle, the plates 16a, 16b translate longitudinally in an alternating fashion along the corresponding portion of the base 12 while the subject S remains comfortably seated in a stable fashion. As a result, a full range of motion of the legs and associated muscles may be automatically achieved, regardless of whether the subject is able to perform the exercise voluntarily, and without the direct application of external force by a motive device (such as a linear cylinder).

Despite the viability of this basic technique for effecting volitional exercise of the upper extremities and induced exercise of the lower extremities with electrical stimulation of the associated muscles being advantageously afforded, it also may be desirable to combine it with a measure of control of the electrical stimulation induced movement based on the volitional movement of the subject (and without the need for active manual control provided by an assistant). To facilitate this result, and with reference now to FIGS. 8 and 9, a particular stimulation controller 100 is also disclosed.

Figure 8:
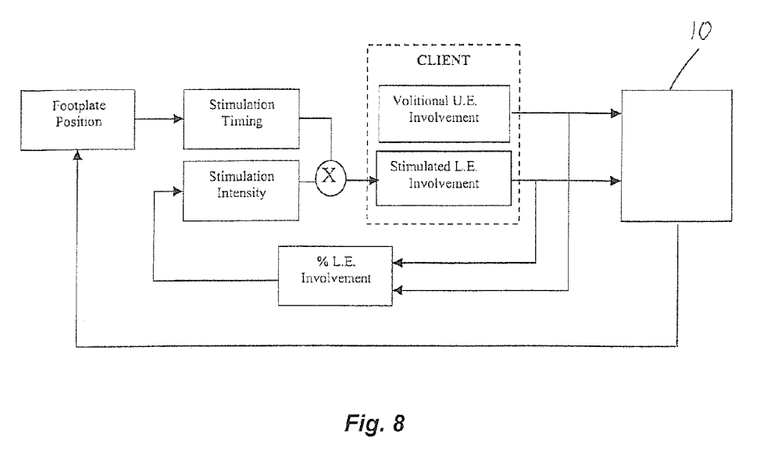
FIG. 8 is a block diagram illustrating stimulation control associated with the device based on one embodiment of the disclosure.
Figure 9:
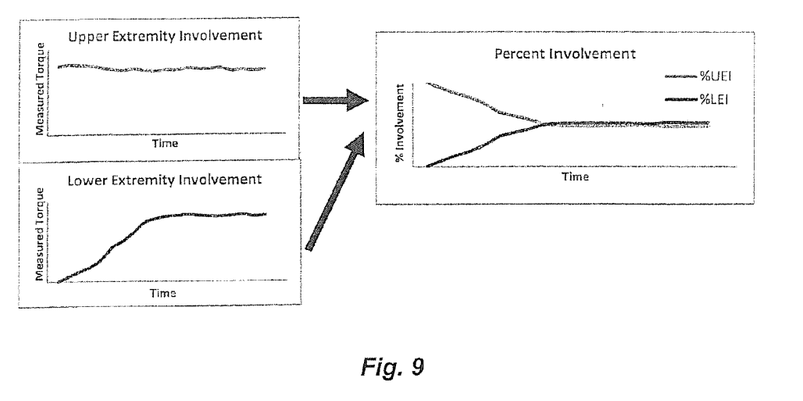
FIG. 9 is a graphical representation of the coordination of upper and lower extremity involvement based on one embodiment of the disclosure.

The controller 100 may be adapted to adjust the stimulation applied throughout the exercise based on a measure of the volitional exercise movement by the subject S. For instance, the level of stimulation applied to the one or more leg muscles may be controlled based on the movement of the subject's upper extremity. Most preferably, the stimulation intensity is adjusted based on a sensed level of force applied by the subject's arms during the recumbent stepping exercise, such as via the sensor (i.e., load cell 19) associated with one or both of the receivers (e.g., handlebars 18a, 18b).

In one particularly preferred approach to using the volitional exercise contributions, the controller 100 is adapted to receive a control variable from an external source of a desired percent lower extremity involvement (% $LEI_{Desired}$), which may be empirically determined or arbitrarily selected based on the particular outcome desired by the subject or clinician. A percent lower extremity involvement (% LEI) may be determined based on measuring the forces applied at the hands and feet (such as via load cell 17) throughout the exercise. Forces are separated into either extraction forces (away from the body) or retraction forces (toward the body). Extraction forces (E) from one hand/foot are combined with retraction forces (R) from the contralateral hand/foot for each timestep (n) throughout an exercise session. Reciprocal forces for both sets of extremities may be combined to represent the upper and lower extremity involvements (UEI, LEI) for that timestep, for example:

During Left Leg Extension:
$E(UEI)_{Right} + R(UEI)_{Left} = UEI_n$
$R(LEI)_{Right} + E(LEI)_{Left} = LEI_n$ During Right Leg Extension:
$E(UEI)_{Left} + R(UEI)_{Right} = UEI_n$;
$R(LEI)_{Left} + E(LEI)_{Right} = LEI_n$ Measurements of extremity forces are then converted to torque measurements ($\tau_n(UEI)/\tau_n(LEI)$) to account for the device's lever arm ($d_{Hand}/d_{Foot}$) between the load cells and the fulcrum point such that hand and foot forces can be compared.

$$UEI_n * d_{Hand} = \tau_n(UEI);$$

$$LEI_n * d_{Foot} = \tau_n(LEI)$$

Finally, the % LEI be calculated as a function of the resultant hand and foot torques.

$$\tau_n(UEI) + \tau_n(LEI) = \tau_n(Total);$$

$$\frac{\tau_n(LEI)}{\tau_n(Total)} = \%\ LEI$$

The controller 100 may monitor % LEI during the exercise, such as for example at each timestep, and adjust the stimulation accordingly (see FIG. 8). As can perhaps best be seen in FIG. 9, controller monitors upper and lower extremity involvement as torque over time. In order to cause % LEI to approach % $LEI_{Desired}$ (shown as 50% in FIG. 9), the controller 100 may elevate the intensity of the electrical stimulation of the lower extremities until the % LEI reaches % $LEI_{Desired}$.

In one particular embodiment, the controller 100 may also utilize algorithms in order to manipulate onset of electrical stimulation based on the footplate position within an exercise cycle and to adaptively control the stimulation intensity based on a percentage of the subject's lower extremity involvement in the exercise. During initial cycles of a session, the upper extremities drive the recumbent stepping exercise. Throughout subsequent cycles, the stimulation control algorithms adjust stimulation intensity such that the lower extremities are actively participating in the exercise in coordination with the upper extremities. The control algorithms continually modify the stimulation intensity to account for changes in volitional upper extremity involvement and lower extremity muscle fatigue.

Figure 10:
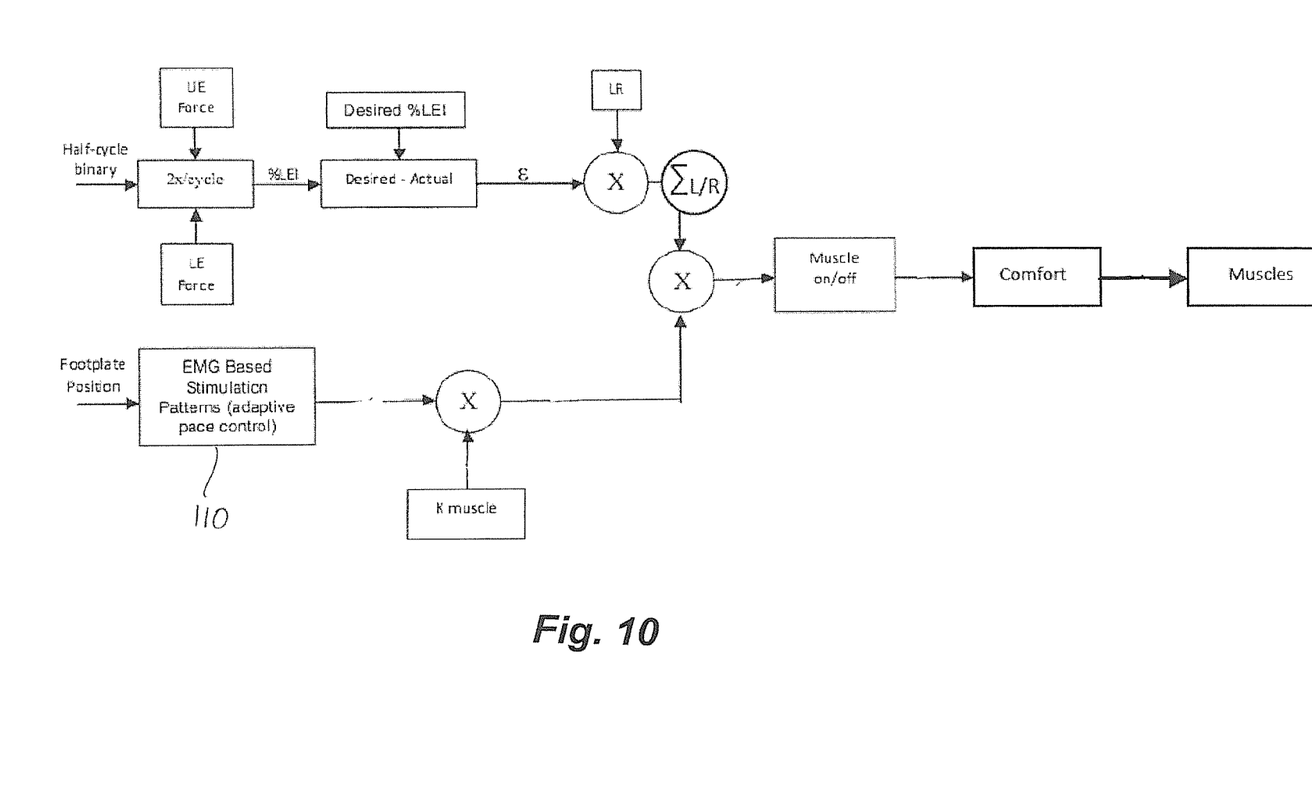
FIG. 10 is a block diagram illustrating stimulation control associated with the device based on another embodiment of the disclosure.

The controller algorithm is graphically represented in FIG. 10. A half-cycle is the movement of a single desired footplate 16a, 16b from 0% to 100% extension. For every timestep during a given half-cycle, % LEI is calculated as above. Upon completion of every half-cycle, the average % LEI (% $LEI_{Average}$) is calculated for the previous half-cycle. The % $LEI_{Average}$ is compared to the % $LEI_{Desired}$ to determine an LEI error value $\epsilon$. Based on the computed LEI error value $\epsilon$, stimulation is adjusted after each half-cycle to theoretically achieve an error of zero. A learning rate variable parameter LR is incorporated into the algorithm to allow a clinician to control the aggressiveness of the change in stimulation (i.e., the rate at which the stimulation accounts for the LEI error $\epsilon$).

The timing of the stimulation is controlled by an adaptive pace stimulation controller 110, which controls timing based on the placement of the footplates 16a, 16b. This controller 110 may apply empirically determined stimulation patterns (which may be synthesized from EMG data taken from normal muscle patterns for six muscles moving the lower extremities during a recumbent stepping exercise) to automatically synchronize the stimulation pattern to the volitional movement by the subject. Indeed, it is possible to use the controller 110 to control the timing of the stimulation pattern at a fixed level of intensity, which may be set by the clinician or subject.

In one embodiment, the position of the handlebars 18a, 18b is constrained along a path of motion analogous to the footplate position in the reciprocal exercise movement. Accordingly, the handlebars 18a, 18b do not move independent of the footplates, but the movements of both elements are coordinated. Because the subject S has independent control over the handlebar position based on his volitional upper extremity movement, the subject controls the pace of the exercise through the pace set by his upper extremities.

The stimulation intensity for a specific muscle group may also be independently controlled, such as by the clinician overseeing the exercise. In FIG. 10, this is represented by the variable $K_{muscle}$, which is used to scale the stimulation pattern accordingly. The resulting scaled stimulation patterns may be multiplied by the summation of the LEI error to produce a controlled, muscle-specific stimulation pattern. The controller may also be adapted to allow the clinician to turn the stimulation applied to an individual muscle on or off, as necessary or desired.

Optionally, and as shown in FIG. 10, the algorithm may further include a "comfort/creep control" feature which may be activated by the subject S in cases of temporary fatigue. Upon activation, the comfort/creep control feature decreases the intensity of the stimulation by a set value (i.e. 5%). The intensity then incrementally rises over a series of cycles until the intensity reaches the original intensity at the time of activating the feature. Upon the intensity returning to said original value, the subject may be allowed to reactivate the comfort/creep control feature. A stall feature may also be provided to determine that the subject has stopped moving and automatically discontinue stimulation. A pick up point feature may also be used to verify that the stimulation pattern is at a zero point when the stimulator begins outputting stimulation, which prevents large instantaneous increases in stimulation. Also, the device may include a feature to discontinue stimulation if both hands are removed from the handlebars.

The foregoing descriptions of various embodiments of the invention are provided for purposes of illustration and not intended to be exhaustive or limiting. Modifications or variations are also possible in light of the above teachings. The embodiments described above were chosen to provide the best application to thereby enable one of ordinary skill in the art to utilize the disclosed inventions in various embodiments and with various modifications as are suited to the particular use contemplated. All such modifications and variations are within the scope of the invention.

The invention claimed is:

1. A device for use in performing an exercise involving at least one lower extremity of a human subject, comprising:
   a base including at least one moveable receiver adapted for engaging the at least one lower extremity;
   at least one stimulator for applying electrical stimulation at a first level to at least one muscle for causing movement of the at least one lower extremity;
   a controller for adjusting the stimulator to apply stimulation to the at least one muscle at a second level based on a volitional movement by the human subject; and
   a sensor for sensing a force exerted by the subject during the volitional movement, and wherein the controller adjusts the stimulator based on the sensed force, wherein the sensor is associated with a second receiver for receiving an upper extremity of the subject.

2. The device of claim 1, wherein the second receiver comprises a handlebar carried by the base, and the sensor comprises a load cell associated with the handlebar.

3. The device of claim 2, wherein the load cell is associated with a grip carried by the handlebar.

4. The device of claim 1, wherein the base includes a pair of receivers, each for receiving one of the lower extremities of the subject.

5. The device of claim 1, wherein the receiver is associated with a sensor for sensing a force resulting from the movement of the lower extremity.

6. A device for use in performing an exercise involving upper extremities and lower extremities of a human subject, comprising:
   a base including a pair of receivers for the upper extremities and a pair of receivers for the lower extremities;
   at least one stimulator for applying electrical stimulation at a first level to at least one muscle for causing movement of the at least one lower extremity; and
   a controller for adjusting the stimulator to apply stimulation to the at east one muscle at a second level based on a volitional movement by the human subject;
   wherein each of the receivers is associated with a sensor for sensing a force resulting from the movement of the corresponding upper or lower extremity.

7. The device of claim 6, wherein the controller is further adapted for adjusting an intensity of the stimulation applied to achieve a desired ratio of force exerted by the upper extremities to the lower extremities.

8. The device of claim 6, wherein the controller is adapted for receiving an input value of a desired lower extremity involvement (LEIDesired) and for measuring an actual lower extremity involvement (LEIActual), and for comparing the LEIDesired with the LEIActual and adjusting the intensity of the stimulator to synchronize LEIDesired with the LEIActual.

9. The device according to claim 1, wherein the controller is further adapted for controlling a rate at which the intensity of the stimulator is adjusted.

10. The device according to claim 1, wherein the controller is adapted to temporarily reduce an intensity of the stimulation and then gradually allow the intensity to increase.

11. The device according to claim 1, wherein the controller provides a stimulation pattern based on the volitional movement.

* * * * *

UNITED STATES PATENT AND TRADEMARK OFFICE
CERTIFICATE OF CORRECTION

| | | |
|---|---|---|
| PATENT NO. | : 8,923,978 B1 | Page 1 of 1 |
| APPLICATION NO. | : 13/450558 | |
| DATED | : December 30, 2014 | |
| INVENTOR(S) | : Hartman et al. | |

It is certified that error appears in the above-identified patent and that said Letters Patent is hereby corrected as shown below:

In the claims

Column 10, line 29, replace "east" with -- least --.

Signed and Sealed this
Fifth Day of January, 2016

Michelle K. Lee
*Director of the United States Patent and Trademark Office*